United States Patent [19]

Lee

[11] Patent Number: 5,735,868

[45] Date of Patent: Apr. 7, 1998

[54] INTRAMUSCULAR STIMULATOR

[76] Inventor: Young H. Lee, 114 Apley Dr., Cherry Hill, N.J. 08003

[21] Appl. No.: 641,516

[22] Filed: May 1, 1996

[51] Int. Cl.$^6$ .................................................. A61B 17/34
[52] U.S. Cl. ................................. 606/189; 606/169
[58] Field of Search ........................... 606/189, 169, 606/167, 181

[56] References Cited

U.S. PATENT DOCUMENTS

| | | | |
|---|---|---|---|
| 4,662,363 | 5/1987 | Romano et al. | 606/189 |
| 5,211,175 | 5/1993 | Gleason et al. | 606/189 |

*Primary Examiner*—Michael Buiz
*Assistant Examiner*—Kevin Truong
*Attorney, Agent, or Firm*—Gary M. Cohen

[57] ABSTRACT

A motor driven needle-poking device for treating patients having chronic muscular pain. The device consists of a motor driven poking tool for mounting a needle, a control unit for adjusting the frequency and the depth of poking, a mechanical swivel arm for holding and positioning said tool, and a remote activation switch for activating the motorized tool. Once the tool is positioned at a proper location of patient's skin by said swivel arm and activated by said switch, the needle pokes the muscle of interest underneath the skin at a constant frequency and at a fixed depth.

18 Claims, 3 Drawing Sheets

INTRAMUSCULAR STIMULATOR

This invention is concerned with an intramuscular stimulating device for treating pain in muscles.

BACKGROUND OF THE INVENTION

The method intramuscular stimulation (IMS) to treated muscular pain by inserting a needle into the muscle was first developed by Gunn ("Dry needling of muscle motor points for chronic low-back pain: a randomized clinical trial with long-term follow-up", Spine, Volume 5, Number 3, pp 279–291, 1980). The method has also been used by others, for example, Chu ("Dry needling in myofascial pain related to lumbosacral radiculopathy", European Journal of Physical Medicine and Rehabilitation, Vol. 5, No. 4, pp 106–121, 1995). A detailed method of the treatment is described by Gunn ("Treating myofascial pain: intramuscular stimulation for myofascial pain syndromes of neuropathic.

Briefly, the method involves inserting a fine needle, similar to an acupuncture needle, into the involved muscle and stimulating the muscle by repeatedly moving the needle back and forth linearly within the muscle. By "back and forth" in this disclosure it is meant that the needle is pushed linearly into the muscle then partially withdrawn linearly and then pushed in again along the same linear path of penetration. This action is repeated many times at each of several muscular sites. For brevity, thin needle manipulation will be referred to as "poking" henceforth in the remainder of the disclosure.

The involved muscle is usually tightly contracted. This tightness of the muscle tends to apply severe pressure or pinching to the nerve fibers within the muscle, thereby causing chronic pain. When the contracted muscle is made to relax by repeated treatments of this intramuscular stimulation, the pain subsides eventually. The frequency of the treatment depends on the severity of muscle contraction. Severely contracted muscle requires frequent treatment over long time periods whereas the frequency will be much less for lightly-injured muscles. The intramuscular stimulation treatment is most usually performed at multiple points to be effective.

Although the method developed by Gunn and used by others is quite effective in treating patients with chronic muscular pain, the method itself is self-limiting because of its detrimental effects on the physician administering the treatment. To treat a patient, the physician pokes a needle manually into the injured muscle at a rate of approximately one to two times per second. Usually, a treatment session lasts about 45 minutes. This means that the total number of manual pokings amounts to 2,700 to 5,400 times per session. Suppose a physician treats eight patients per day—each with a 45 minute treatment session. This means that the total number of manual pokings will be 21,600 to 43,200 times per day. This enormous amount of repeated manual poking causes severe strain and pain to the shoulder and neck muscles of the physician and in time damages the physician's muscles. Unless the physician is treated (frequently by the IMS treatment, ironically), eventually he/she will not be able to perform the treatment any more. This is why the method is considered self-limiting.

Also, the manual poking of the needle is very painful to the patient. This is presumably because the needle is constantly accelerated and decelerated during manual insertion and withdrawal during the course of the treatment. Usually, the patient must be premeditated with narcotics to avoid excessive discomfort during the treatment.

SUMMARY OF THE INVENTION

This invention discloses an automated, motor driven, needling instrument for administering an intramuscular stimulation treatment to patients suffering from chronic muscular pain. This invention replaces manually operated muscle stimulators with a muscle stimulator which is mechanically linked to an electrically-driven motor which in turn is electrically connected to a programmable control unit. Specifically, the invention discloses an intramuscular stimulator needling device which is mechanically linked to a linear action motor allowing the motor to drive the needle continuously back and forth within the muscle in a controlled manner. The person administering the treatment can hold the instrument steadily at a treatment site while the motor provides controlled, uniform, back and forth linear motion to the intramuscular stimulator needle at fixed penetration depths. This eliminates to a great degree, the tedious, muscle straining labor involved in the usual manual poking treatment, thereby relieving the physical burden of the person administering the treatment.

For extended intramuscular stimulation treatment sessions, even holding the mechanized needling device steadily by hand becomes burdensome. This invention further eliminates this extra strain by using a mechanical swivel arm to hold the stimulator needling instrument. This mechanical swivel arm is extendible, moves in all directions, and holds the needling device in place. Also, a foot switch can be provided to turn the motor on and off remotely. In this way the intramuscular stimulation treatment can be performed with minimal physical effort to avoid muscle injury to the person administering the treatment.

A major additional advantage in using this invention is in the dramatic reduction in the pain experienced by the patient during the treatment. With the conventional manual poking, the needle is accelerated and decelerated frequently because of the uneven manual poking action. This transient shearing action is enormously painful to the patient. The constant speed and uniform motion provided by this invention eliminates the pain very significantly—clinical tests showed about a 75% reduction in pain experienced by the patient during treatment.

Thus the principal object of this invention is to provide an automated, mechanized, intramuscular stimulator needling device which is mechanically linked to a programmable, electrical, control motor, which produces uniform back and forth motion to the stimulator needle at fixed penetration depths.

A further object of this invention is to provide an intramuscular stimulator needling device whose motion is provided by an electrical motor in a uniformly controlled manner, relieving the medical operator of the muscular strain of having to provide this motion manually.

A further object of this invention is to provide a motor-driven and controlled intramuscular stimulator needling device which provide the patient with a safer, more effective, uniform, and less painful treatment.

A further object of this invention is to provide a means for holding this intramuscular stimulator needling device steadily and accurately at the treatment site with less strain on the medical operator.

These and other objects will be apparent to those skilled in the art from the description and claims which follow.

BRIEF DESCRIPTION OF THE DRAWINGS

The invention may take form in various arrangements of parts. The drawings are only for the purpose of illustrating a preferred embodiment of the invention and are not to be construed as limiting it.

DETAILED DESCRIPTION OF A PREFERRED EMBODIMENT

Figure 1:
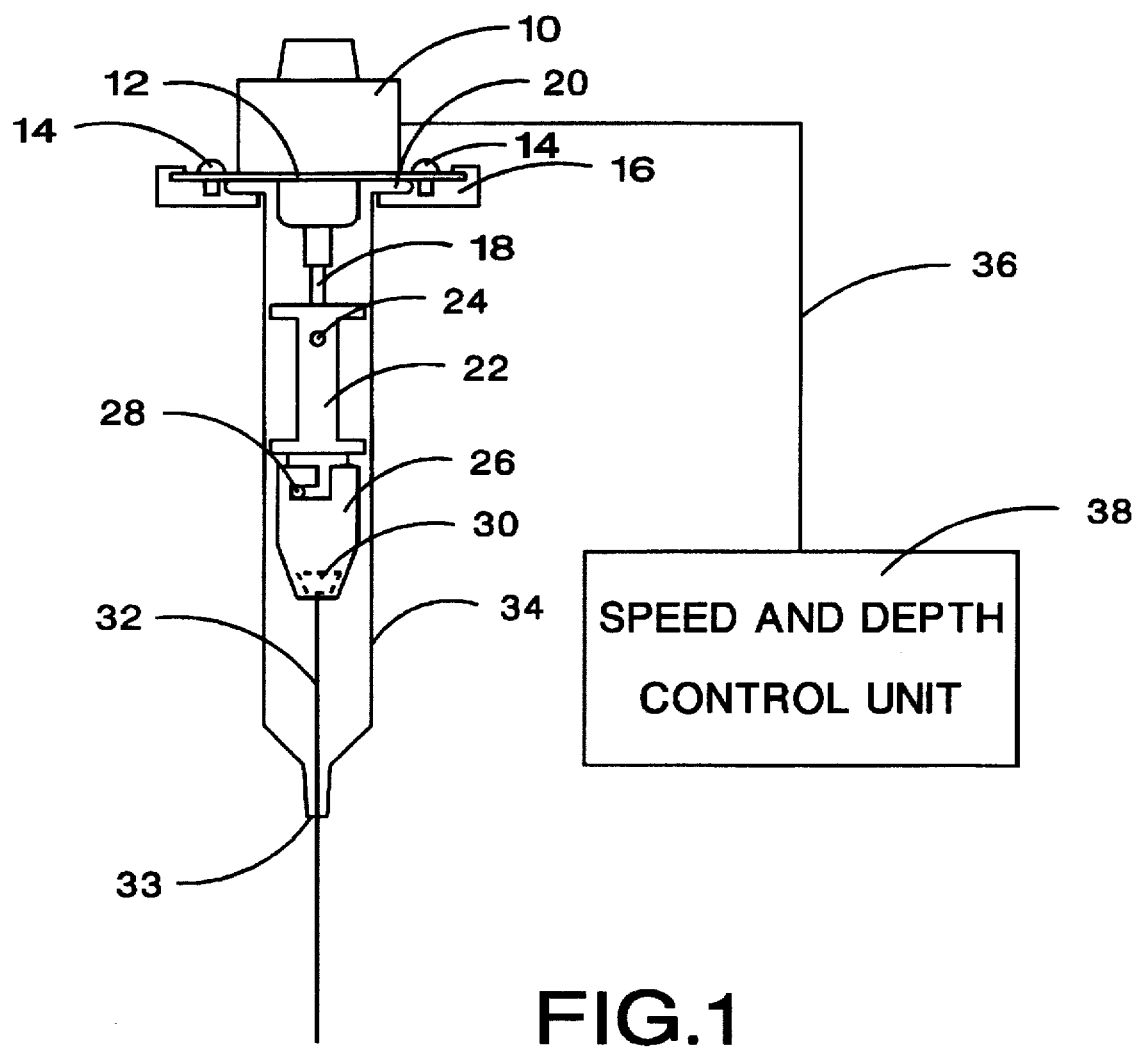
FIG. 1 shows a side view of the intramuscular stimulator needling device and its connection to a control unit.

FIG. 1 shows the structure of motor driven intramuscular stimulator needling device, (IMS needling device), and its connection to control unit 38 for adjusting the speed and depth of poking. The two units are connected electrically by a wire 36. When treating a patient, the operator positions syringe body 34 above the skin of the patient, directly above the involved muscle. The syringe body 34 has a portal 33 which allows needle 32 to move in and out freely. The control unit 38 is then turned on to energize the needle movement. Once energized, the needle 32 moves back and forth at a frequency set by the control unit 38. The length of needle movement—i.e., the depth of poking—is also determined by the control unit 38 which is preset. The needle 32 penetrates the skin and starts stimulating the target muscle repeatedly until the needle is withdrawn.

The IMS needling device consists of five major parts: a linearized motor 10, syringe holder 16, syringe body 34, plunger 22, needle holding cap 26, and needle 32. The linearized motor 10 has internal gears that convert the rotational motion of the motor into the linear motion of a shaft 18. A linear motor manufactured by Philips Technologies, Cheshire, Conn. is an example of such a motor. The direction of motor rotation determines the direction of the linear movement. For example, when the motor turns clockwise, the shaft 18 moves downward, whereas the shaft 18 moves upward when the motor turns counterclockwise. Control unit 38 sends the motor 10 both the movement signal and the direction signal via electrical lines 36. Syringe holder 16 has the function of retaining syringe body 34. The syringe holder 16 is a machined part fixed to the base plate 12 of the motor 10 by two retaining screws 14 and forms a housing for syringe base plate 20. The syringe holder 16 preferably made of Plexiglas is machined so that the syringe body 34 can be easily attached and detached by a twist-lock mechanism. The syringe body 34 is made of a transparent polymer material so that the inner motion of the needle 32 can be seen from outside of the syringe body. A commercially available, 10 cc size disposable syringe is a representative example for the syringe part. Plunger 22 is a machined part made of a plastic material such as Lexan, Nylon, or Teflon, and has the role of linking motor 10 and needle 32. As shown in FIG. 1, one side of the plunger 22 is attached to motor shaft 18 by a set screw 24. The opposite side of the plunger 22 has a retaining pin 28 for holding needle holding cap 26 by a twist-lock mechanism. The needle holding cap 26 is a machined part that has the role of holding the needle 32 firmly in place, aligned along the axis of the shaft 18, during treatment of patients. The upper end of cap 26 has a twist-lock slot, as shown in FIG. 1, for rapid replacement of needles. The lower end of cap 26 has a machined hole to fit the head 30 of needle 32. The needle is of very small diameter (such as an acupuncture needle) for efficient insertion into the skin and muscle tissue. The needle must have a plastic head 30 for convenience of holding.

In the IMS needling device consisting of parts 10 through 32, replaceable parts are syringe body 34, needle holding cap 26, and needle 32. These parts have to be sterilized each time before a new patient is treated with them. To replace a needle 32, the syringe body 34 is first twisted off from the syringe holder housing 16. Then, the holding cap 26 is twisted off from the plunger body 22 and the needle 32 is finally taken out from the holding cap 26. These steps are reversed to mount a needle.

Figure 2:
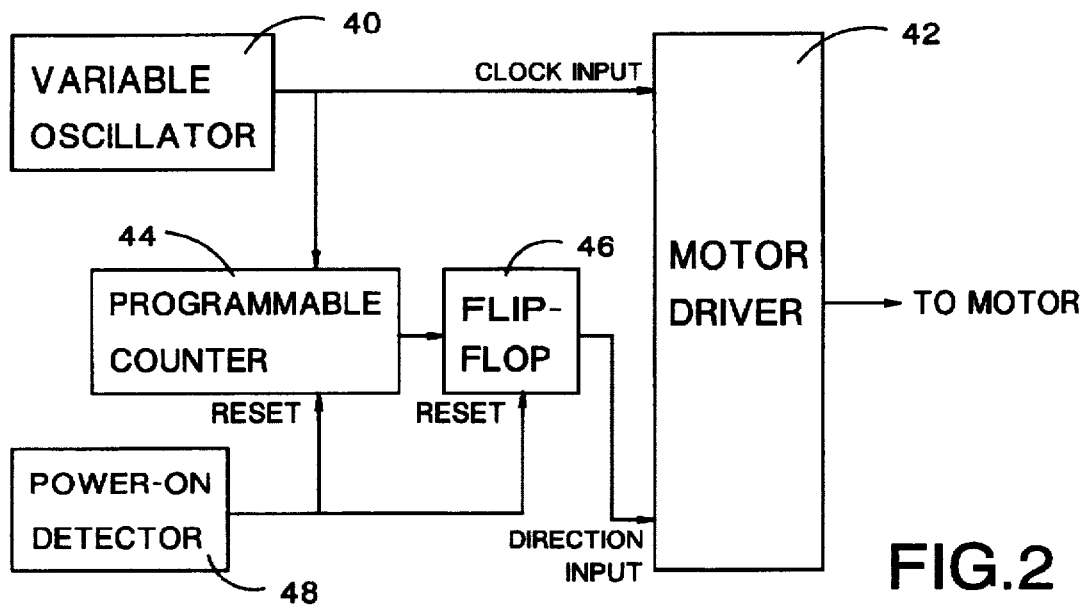
FIG. 2 shows a functional diagram of the speed/depth control unit.

Speed and depth control unit 38 is a battery or electrically powered electronic unit that has the function of controlling the linear movement of the motor in terms of speed and length of stroke. As shown in FIG. 2, the control unit consists of five main circuit blocks: variable oscillator 40; motor driver 42; programmable counter 44; flip-flop 46; and power-on detector 48.

Figure 3:
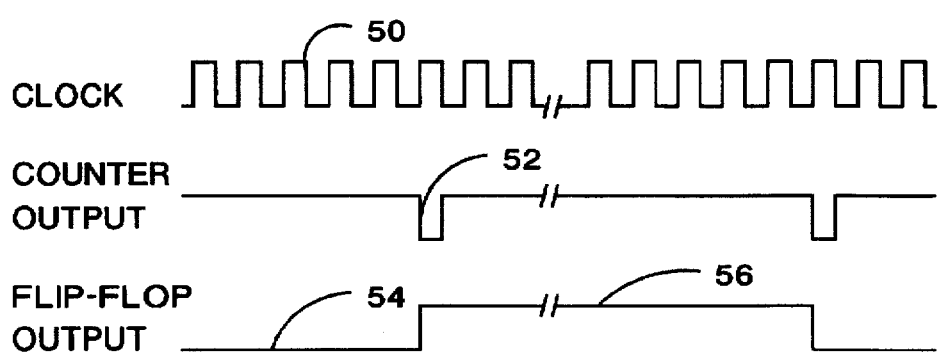
FIG. 3 shows the logic timing diagram of the control unit.

Variable oscillator 40 generates a square wave signal such as that shown in FIG. 3, item 50. The frequency of the clock signal is adjustable. The variable oscillator can be made either from a crystal-based oscillator circuit or from a timer integrated circuit chip, such as 555 timer chip.

The motor driver 42 has the function of sending the necessary power to the motor 10 for moving shaft 18 linearly. To do this, motor driver 42 requires a clock input and a direction input. The clock input should be a pulse train such as the one shown in FIG. 3, item 50. Each pulse moves motor shaft 18 by a fixed distance. Therefore, if one pulse moves the motor shaft by 0.02 inches, then 20 pulses are required to move it 0.4 inches. The frequency of the clock pulse determines the speed of the movement. For example, if the clock rate generated by variable oscillator 40 is 100 Hz, then motor shaft 18 will move 2 inches per second when each pulse moves the shaft by 0.02 inch. Motor driver 42 also requires a direction input. The direction input is a logic signal that determines the direction of the shaft movement. For example, when the logic signal is high, the movement of the motor shaft is in forward direction whereas, when it is low, the movement is in reverse direction.

Programmable counter block 44 functions as a source for generating the direction signal for motor driver 42. The counter block has a preset count value. This preset count value is decremented by one as each clock pulse is counted by the counter. When the terminal count is reached, programmable counter 44 generates a logic pulse corresponding to one clock pulse (as shown in FIG. 3, item 52). This logic pulse signal is fed to flip-flop circuit block 46. After the terminal count, programmable counter 44 re-loads the preset count value and repeats the same operation to generate the next pulse signal. The preset count value is programmed by the operator.

Flip-flop circuit block 46 is a logic circuit that changes its output logic level upon accepting an input pulse signal. This is shown schematically in FIG. 3. When there is no pulse signal input from programmable counter 44, the output of the flip-flop is low, as shown by item 54 of FIG. 3. When the flip-flop receives a logic pulse, its output changes the logic state as shown by item 56 of FIG. 3. Because programmable counter 44 generates a clock pulse at the terminal count, the output of the flip flop changes its logic state at the end of each terminal count. This means that the directional input to the motor driver 42 changes at every terminal count of programmable counter 44. This in turn changes the movement direction of motor shaft 18.

Power-on detector block 48 generates a logic pulse when the power is turned on. This pulse is fed to the reset inputs of programmable counter 44 and flip-flop block 46. Upon receipt of this pulse, programmable counter 44 and flip-flop 46 reset their outputs such that control unit 38 starts its operation at the same logic state every time the power is turned on.

Figure 4:
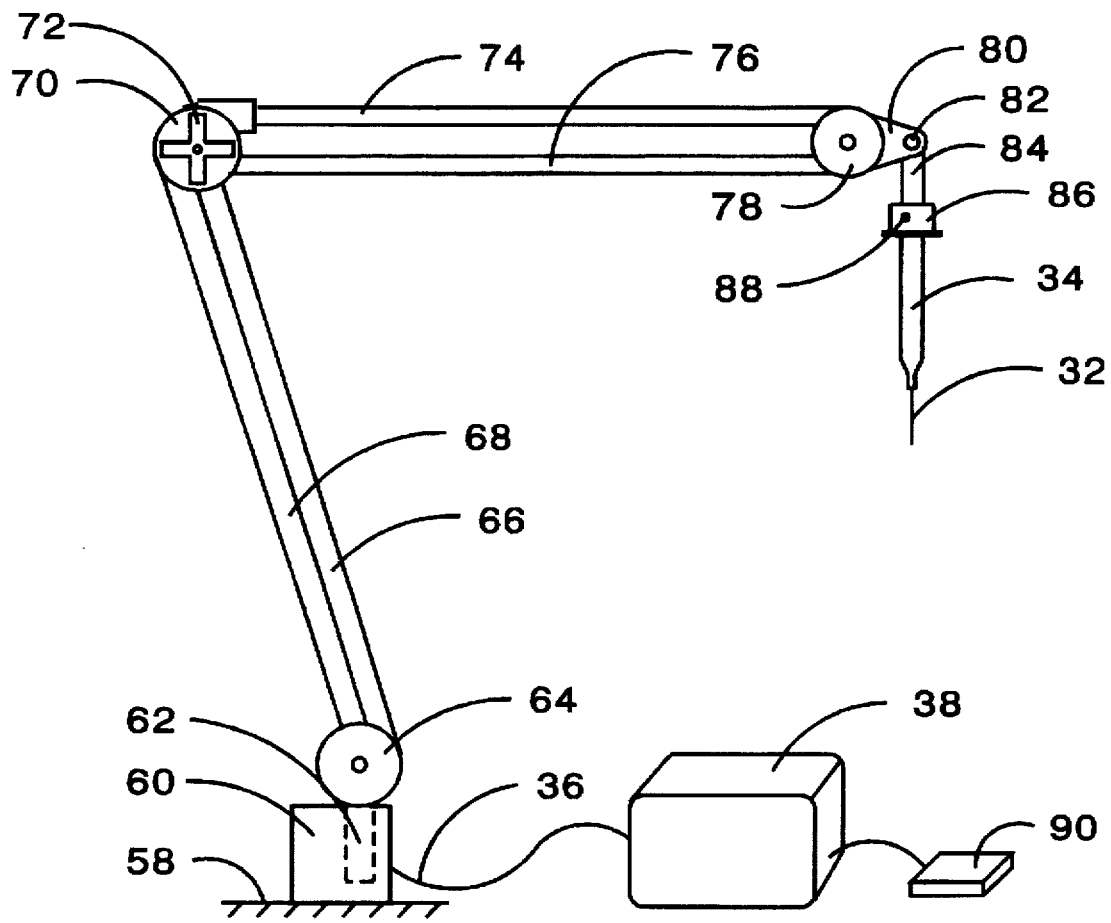
FIG. 4 shows the overall arrangement of the intramuscular stimulator device.

For intramuscular stimulation treatment, the IMS needling device shown in FIG. 1 can be held by hand by grasping syringe body 34. However, holding the device in a fixed position for an extended period becomes burdensome to the operator. This physical effort is much relieved by using a mechanical swivel arm to hold the device while the operator merely has to move the swivel arm to position the needling device at the desired treatment position. This arrangement is shown in FIG. 4. Instead of hand holding the syringe body 34, it is held by a mechanical swivel arm consisting of parts 60 through 82. The IMS needling device shown in FIG. 1 is attached to tool holder assembly 80 via motor holder housing 86. The holder housing 86 is a machined part preferably made of aluminum. The head part of the motor 10 is placed in the holder housing 86 and fixed with a set screw 88. The holder housing 86 has a short handle 84 that is attached to tool holder assembly 80 by a set screw 82.

The swivel arm allows positioning of the needling device in all directions within the reach of the arm. The arm has three joints: base joint 64, middle joint 70; and end joint 78. There are two beams between joint 64 and joint 70: upper arm beam 66 and lower arm beam 68. Also, there are two beams—upper forearm beam 74 and lower forearm beam 76—between middle joint 72 and end joint 78. The joints lows bending and stretching of the arm beams. The stiffness of bending and stretching is adjusted by lightening or loosening screw 72. The swivel arm is fixed on a solid surface 58 by a mounting base 60. The base 60 has a hole to accept base pin 60. This arrangement allows 360° rotation of the swivel arm. The material of construction for the swivel arm parts is preferably steel.

The forearm beam 76 and arm beam 66 are hollow and carries the electrical wire from the motor. The electrical connection to control unit 38 is made at base 60 of the swivel arm as shown in FIG. 4. A foot switch 90 is connected to control unit 38 for starting and stopping of the motor remotely.

When the IMS needling device is attached to the swivel arm as shown in FIG. 4, needle 32 can be moved freely in all directions. To treat a patient, the needle is first moved by extending the mechanical swivel arm to the position on the patient's skin under which the muscle to be treated lies. After the positioning, foot switch 90 is pressed to activate control unit 38. In this way, the use of operator's hand and muscles is minimized. This enables the operator to practice the intramuscular stimulation treatment for an extended time without injuring him/herself.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What I claim is:

1. A motor-driven intramuscular stimulation needling device for relieving chronic muscular pain, comprising a needle and an electrically powered motor for inserting the needle into an affected muscle so that said needle produces a repeated, controlled motor-driven back and forth poking of the muscle, an energy source for energizing said motor, and a mechanical linkage linking said needle to said motor for causing a linear back and forth motion to said needle when said motor is energized.

2. The device of claim 1, wherein said mechanical linkage includes a shaft having means for attaching said needle and means for connection to said motor in a linear relation so that said motor moves said shaft back and forth in a controlled, linear motion for imparting the linear back and forth motion to said needle.

3. The device of claim 2, wherein said needle and said shaft are coupled by a detachable connection.

4. The device of claim 3, wherein a sterilized needle is detachably connected to said shaft.

5. The device of claim 2, further comprising a tubular housing for receiving said needle and said shaft, said tubular housing having means for attaching one end of said housing to said motor and a portal at an opposite end of said housing for passing said needle freely in and out of said housing, wherein said housing is of a sufficient strength to allow said housing to be grasped firmly during use.

6. The device of claim 5, wherein said housing is made of a strong transparent material.

7. The device of claim 1, further comprising an electrical control unit for electrically controlling said motor, said control unit having means for producing and maintaining an adjustable, fixed frequency for poking of the needle and an adjustable depth for poking of the needle responsive to electrical control signals transmitted to said motor.

8. The device of claim 7, wherein said control unit has programmable means for controlling the frequency and the depth of said needle when in motion.

9. The device of claim 7, wherein said control unit is coupled with said motor by an electric cord.

10. The device of claim 9, wherein said control unit further includes a foot pedal having an on-off electric switch for starting and stopping said motor.

11. The device of claim 1, wherein said motor is energized by a battery.

12. The device of claim 1, further comprising a mechanical swivel arm for holding said device in a fixed position at a treatment site.

13. The device of claim 12, wherein said swivel arm is movable in all directions.

14. A method for relieving chronic muscular pain using an intramuscular stimulation treatment including insertion of a needle into an affected muscle and poking the muscle repeatedly with the needle, wherein said method is less uncomfortable for a patient and less of a strain on a treatment administrator, said method comprising the steps of applying at a treatment site a motor driven needle stimulator device including a needle and an electrically powered motor for driving the needle in a uniform, controlled back and forth linear motion having a fixed distance and frequency for repeatedly inserting said needle into the muscle, and energizing said motor while holding said device at the treatment site for a required treatment time interval.

15. The method of claim 14, further comprising the steps of providing the motor driven needle stimulator device with an adjustable swivel arm for holding said device at the treatment site in a fixed position, and grasping said device with said swivel arm while applying said device to the treatment site for the required treatment time interval.

16. The method of claim 14, further comprising the step of programming said device to control the frequency of the back and forth linear motion of said needle.

17. The method of claim 14, further comprising the step of programming said device to control the depth of the back and forth linear motion of said needle.

18. The method of claim 14, further comprising the step of detachably connecting a sterilized needle to said device.

* * * * *